United States Patent [19]

Raines

[11] Patent Number: 4,787,898
[45] Date of Patent: Nov. 29, 1988

[54] VENTED NEEDLE WITH SIDEPORT

[75] Inventor: Kenneth C. Raines, Bethlehem, Pa.

[73] Assignee: Burron Medical Inc., Bethlehem, Pa.

[21] Appl. No.: 48,824

[22] Filed: May 12, 1987

[51] Int. Cl.$^4$ .............................................. A61M 5/00
[52] U.S. Cl. .................................... 604/411; 606/405; 606/126
[58] Field of Search ............... 604/411, 405, 35, 45, 604/126

[56] References Cited

U.S. PATENT DOCUMENTS

| | | | |
|---|---|---|---|
| 3,662,752 | 5/1972 | Yokoyama | 604/411 |
| 3,797,521 | 3/1974 | King | 604/405 X |
| 3,938,520 | 2/1976 | Scislowicz et al. | 604/405 |
| 4,211,588 | 7/1980 | Raines | 604/405 X |
| 4,596,552 | 6/1986 | De Vries | 604/35 X |

Primary Examiner—Stephen C. Pellegrino
Attorney, Agent, or Firm—Shoemaker and Mattare, Ltd.

[57] ABSTRACT

A vented needle with sideport comprising a main body housing having dual input ports at substantially right angles to each other. An integral needle structure having a central aperture therethrough being generally in the same axial alignment as one input port and transversely to the other port. A tubular sleeve around the projecting needle for providing a second fluid flow path externally thereof. The needle preferably has a longitudinal groove therein for increasing the fluid flow along the circumference of the needle. The device is designed so that the needle is longer than the tubular sleeve and, thus, air can be passed therethrough without danger of any air being inputted to the liquid flow of the shorter tubular sleeve liquid flow passageway. A hydrophobic air vent filter preferably is connected to the air input of the device.

The method of assembly of this vented needle with side port is also part of this invention.

11 Claims, 2 Drawing Sheets

VENTED NEEDLE WITH SIDEPORT

BACKGROUND OF THE INVENTION

1. Field of the Invention

This invention relates generally to devices for drug reconstitution and especially to the inputting structure for effecting the desired procedure.

2. Description of the Prior Art

A common problem of known devices for drug reconstitution is that the devices known and being used today utilize two basic concepts. According to one concept, devices having plastic spikes with separate holes for fluid and air are employed. However, such devices cannot be made small enough in diameter to prevent damage to small 13 millimeter rubber stoppers with which it would be desirable to use same. In a second concept, hypodermic needles having a vent sleeve around the needle have been used. This design will easily puncture the smaller stoppers, but because the vent sleeve itself is shorter than the needle for the fluid path, air will be sucked into the fluid path during the aspiration process. This is obviously undesirable.

Existing prior patents which may be pertinent to the present invention are as follows:

| | |
|---|---|
| 2,409,343 | 10/15/46 |
| 3,662,752 | 5/16/72 |
| 4,505,709 | 3/19/85 |
| 4,507,113 | 3/26/85 |
| 4,534,758 | 8/13/85 |
| 4,610,683 | 9/9/86 |

In the Curtis U.S. Pat. No. 2,409,343, an arrangement is disclosed wherein the large cannula is utilized for the air passageway, and the smaller cannula associated therewith is utilized to facilitate aspiration of the liquid contents from a bottle. However, this device has parallel tubes which are closely contiguous as compared to the present invention having concentric tubes that do not touch. In the Curtis device, it is also disclosed that the tubes can be interchanged with each other. In the present invention, the liquid and air channels are separate, are fixed in place, and cannot be interchanged. Furthermore, in the Curtis device, each tube has an open end for the attachment of tubing; while in the present invention, molded fittings specifically for the purpose of attachment of a syringe and hydrophobic filter are provided.

The other patents listed have various arrangements involving cannulas or spikes and associated air passageways. However, none of the known prior art devices offer the new and novel features of the present invention.

SUMMARY OF THE INVENTION

An object of the present invention is to provide a vented needle with sideport for injection of fluid into and aspiration of the reconstituted drug from a closed container with rubber stopper.

Another object of the present invention is to provide a device for the reconstitution of drugs wherein one fluid flow path is provided for liquid by connection to a syringe and a second flow path is provided concentric therewith for flow of air through a hydrophobic filter.

A further object of this invention is to provide a vented needle with sideport wherein concentric passages project from a body housing with one flow path being provided for air and the other flow path being provided for liquids.

A still further object of the present invention is to provide a new method of assembly of an improved vented needle with sideport.

Yet another object is to provide a body having a main input for liquid from a syringe and a transversely mounted input for air with the respective exits from the respective inputs consisting of two concentric outlets from the body. One outlet is shaped in the form of a needle and the other is shaped as a tube concentrically mounted therearound.

The present invention has a number of new and novel features. Among them are a main body housing having an input for a hypodermic syringe and a second transversely mounted input for connection to a hydrophobic air vent filter. The air input connects with a needle-type projecting outlet having a sharp pointed tip and the liquid input connects with a tubular sleeve concentrically mounted around the needle. Thereby, a flow of liquid can take place longitudinally and concentrically around the air flow needle. Preferably, a groove is provided in and longitudinally of the needle to increase the liquid flow capacity of the fluid outlet. Similarly, the needle projection has an angled sharp tip for ease of puncture of the small rubber stoppers in drug containers.

Another important feature of the present device is that the center needle having an air flow aperture longitudinally therethrough is longer than the surrounding liquid flow concentric sleeve. Thus, air cannot be sucked into the liquid path during an aspiration process when using the present invention.

The method of assembly of the vented needle with sideport of the present invention really facilitates the ease and speed of manufacturing the device itself.

These together with other objects and advantages which will become subsequently apparent reside in the details of construction and operation as more fully hereinafter described and claimed, reference being had to the accompanying drawings forming a part hereof, wherein like numerals refer to like parts throughout.

DESCRIPTION OF THE PREFERRED EMBODIMENT

Figure 1:
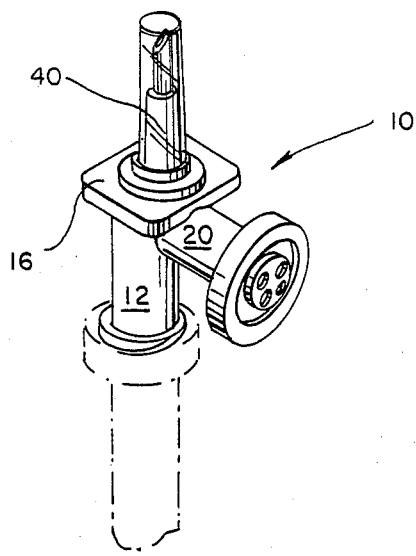
FIG. 1 is a perspective view of the vented needle with sideport of the present invention.
Figure 3A:
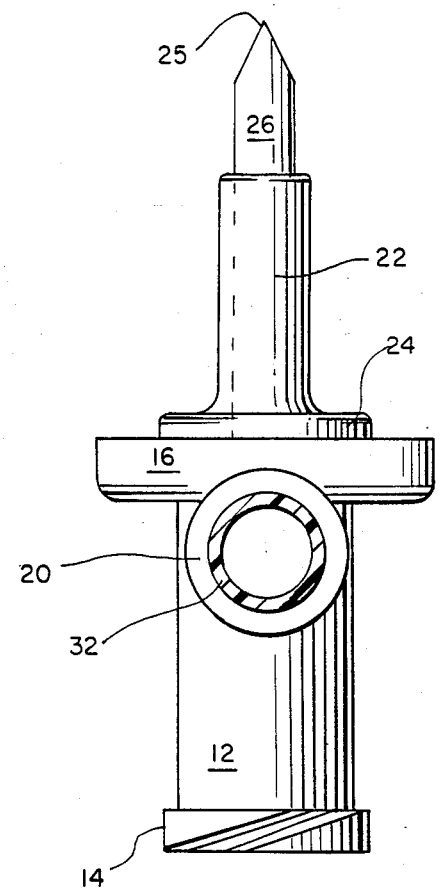
FIG. 3A is an end elevational view in cross-section, taken generally along lines 3A—3A of FIG. 2.

Referring to FIG. 1 of the drawings, reference numeral 10 indicates the device of the present invention. As best seen in the cross-section of FIG. 5, the main body housing 12 has one port 13 internally and longitudinally thereof together with a luer fitting 14 at the end.

An internal passageway for liquid flow LF is provided by this one port 13. Another port 20 is provided in the body 12 at substantially right angles to the one port 13. This second port 20 has an internal passageway 15 for permitting air flow AF therethrough.

Figure 2:
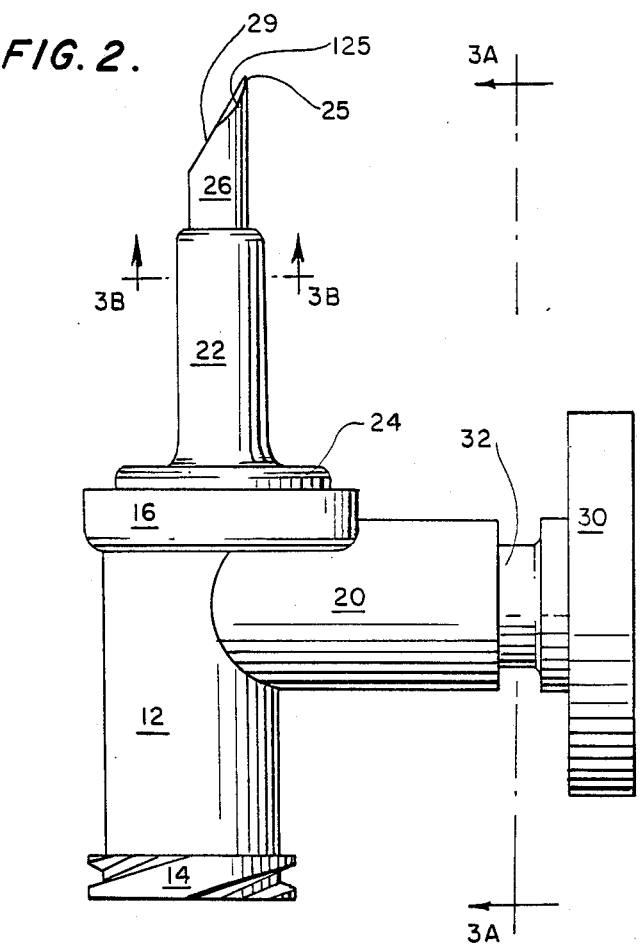
FIG. 2 is a side elevational view of the device of FIG. 1.
Figure 3B:
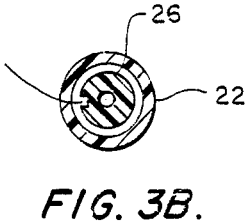
FIG. 3B is a cross-sectional view taken generally along lines 3B—3B of FIG. 2.

A needle 26 is preferably molded integral with the body 12 and is provided with a central longitudinal aperture 27 therethrough. This aperture 27 joins with the air port passageway 15 at central chamber CC inside the body 12. The needle 26 preferably has a very sharp point 25 and a tapered end surface 29. Also, it may be desirable to include slight chamfers 125 along the edges of the end surface 29 as best seen in FIG. 2. The housing 12 includes integrally therewith a flange portion 16 which also joins with and strengthens the transverse port 20.

Figure 4:
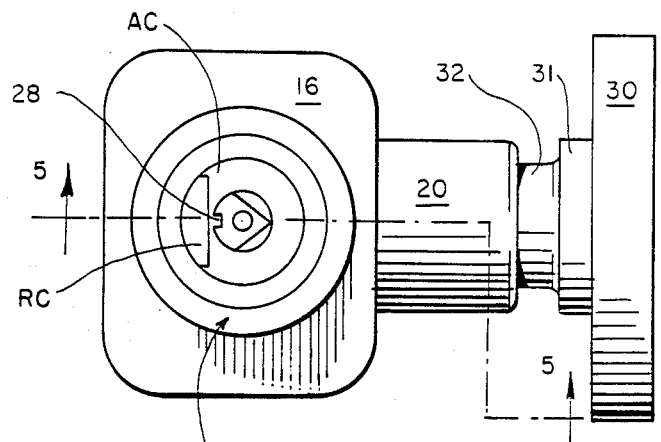
FIG. 4 is a top plan view with the outer liquid flow sleeve being omitted.

Looking at the top plan view of FIG. 4, a circular recess portion 23 is indicated. This recess 23 is for the purpose of receiving the relatively large circular flange portion 24 of the liquid sleeve 22. During assembly of the device, sleeve 22 is placed over the needle 26 and glued into place by suitable adhesive AD, or plastic welding, so as to form a permanent integral connection with the flange end 16 of housing 12.

Figure 5:
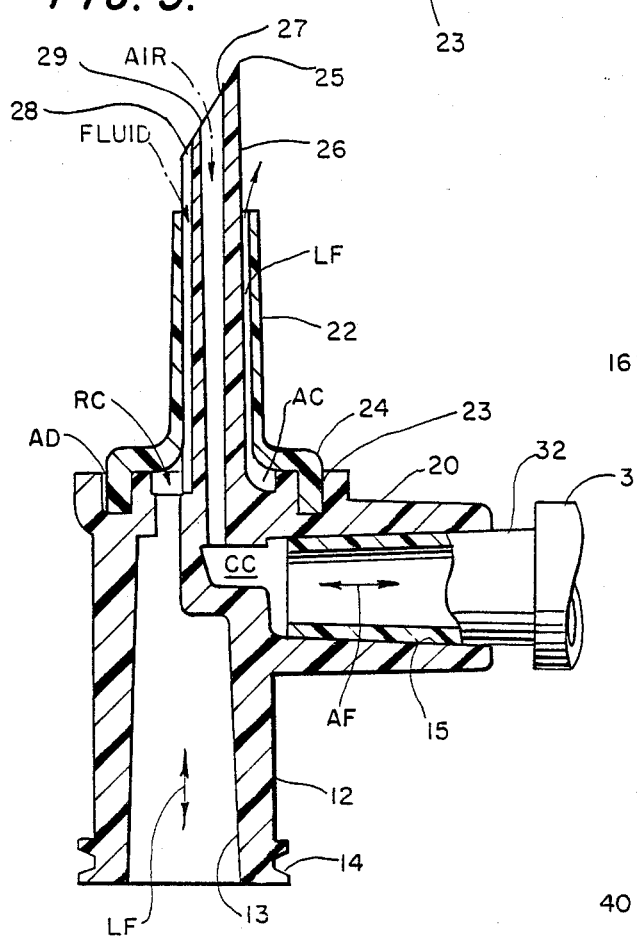
FIG. 5 is a side elevational view, partly in cross-section, taken generally along lines 5—5 of FIG. 4, but with the liquid flow sleeve having been added.

As best seen in the cross-section of FIG. 5, by the sleeve 22 being concentric to needle 26 and slightly larger in internal diameter than the outer circumference of needle 26, a liquid flow path LF is provided. In order to increase the overall liquid flow capacity of the device, a longitudinal channel or slot 28 also preferably is provided in needle 26.

Also provided in the flange portion 16 of the housing is an axial channel AC which joins with a rectangular channel RC which, in turn, joins with the liquid flow port 13 of the body housing.

For most applications, preferably a hydrophobic air vent filter 30 will be connected by projections 31 and 32 to the air port 15 of the device.

As can be easily visualized by looking at the cross-section of FIG. 5, air can move through the port 15, the central chamber CC and the needle aperture 27 freely in either direction while liquid can flow through liquid port 13, rectangular recess RC, axial recess AC, and along the outer circumference of needle 26 and within the confines of the sleeve 22. Because the needle 26 is substantially longer than the sleeve 22, the possibility of getting air mixed with the liquid is eliminated.

Figure 6:
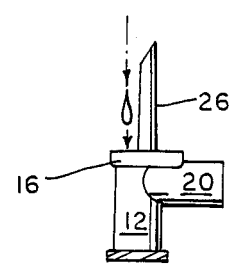
FIGS. 6–10 are sketches of the method of assembly of the present device.
Figure 7:
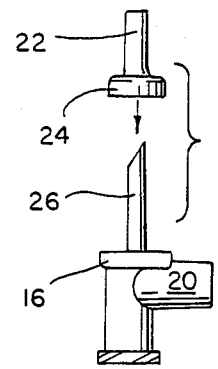

The method of assembly of the present device is also part of this invention. As depicted in FIGS. 6-10 in schematic form, the steps of this method will be described. After molding the main body housing 12 complete with integral flange 16 and transverse air port 15, 20 with air needle 26, a solvent is applied to the recess 23 in the flange 6. After the application of the solvent as depicted in FIG. 6, the tubular liquid sleeve 22 with flange 24 is placed over the needle 26 and the flange 24 pressed into the recess 23 of flange 16. The solvent already applied will assure that the sleeve becomes a permanent part of the body housing.

Figure 8:
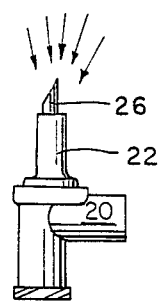
Figure 9:
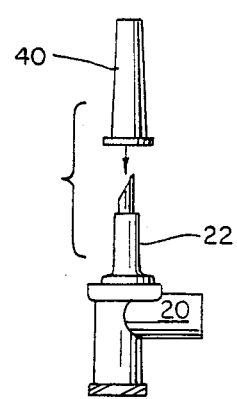
Figure 10:
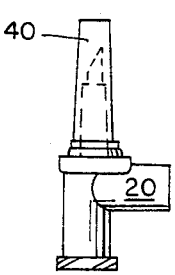

Next, the needle tip 26 is sprayed with silicone as depicted in FIG. 8 and then a guard 40 is loaded or placed over the sleeve 22. The final step is to press and hold the guide 40 in place until the silicone has dried, thus substantially completing the structure. However, in many cases, a hydrophobic air vent filter 30 is also assembled and sold with the device already described and, in such cases, the filter would then be added to the transverse air port 20 before final packaging of the overall structure.

The foregoing is considered as illustrative only of the principles of the invention. Further, since numerous modifications and changes will readily occur to those skilled in the art, it is not desired to limit the invention to the exact construction and operation shown and described, and accordingly all suitable modifications and equivalents may be resorted to, falling within the scope of the invention.

I claim:

1. A vented drug reconstitution device comprising:
   a main body having two ports at substantially right angles to each other therein;
   said body having a needle with a central aperture for air flow therethrough substantially in line with one port for liquid, but not contiguous therewith;
   the other port in said body being transverse to the needle and one port, and contiguous with the central aperture of the needle for air flow therethrough; and
   tubular means affixed to the body substantially concentric with said needle for effecting liquid flow therealong from said one port.

2. The device of claim 1, wherein the components are molded of plastic.

3. The device of claim 2, wherein said transversely mounted air flow port has a hydrophobic air vent filter connected thereto.

4. The device of claim 3, wherein said one port for liquid flow is designed for reception of a hypodermic syringe therewith.

5. The device of claim 4, wherein luer fittings are provided with each of the respective input ports.

6. The device of claim 1, wherein said transversely mounted air flow port has a hydrophobic filter connected thereto.

7. The device of claim 1, wherein said one port for liquid flow is designed for reception of a hypodermic syringe therewith.

8. The device of claim 1, wherein luer fittings are provided with each of the respective ports.

9. A method of assembly of a vented needle, comprising the following steps:
   molding from a plastic material a needle body having a longitudinal port, a needle in substantial alignment with the longitudinal port and defining a flow passage therein, and an annular recess around a base portion of said needle;
   applying a solvent to the recess as formed in said body; and
   seating one end of a tubular sleeve in said recess so that the sleeve extends concentrically with the needle, whereby the sleeve is permanently affixed to the body and defines an annular flow passage around said needle separate from the flow passage defined within the needle.

10. The method of claim 9, including the further steps of:
    spraying the needle tip with silicone;
    loading a guard cap over the needle and sleeve assembly; and
    pressing and holding the guard cap in place until the silicone lubricant dries.

11. The method of claim 10, including the further step of adding a filter structure to one of the ports of the body housing.

* * * * *